United States Patent
Guo et al.

(10) Patent No.: US 8,349,854 B2
(45) Date of Patent: *Jan. 8, 2013

(54) SALTS OF 4-ANILINE QUINAZOLINE DERIVATIVE

(75) Inventors: Jianhui Guo, Shanghai (CN); Yong Jiang, Shanghai (CN)

(73) Assignee: Shanghai Allist Pharmaceuticals, Inc. (CN)

( * ) Notice: Subject to any disclaimer, the term of this patent is extended or adjusted under 35 U.S.C. 154(b) by 0 days.

This patent is subject to a terminal disclaimer.

(21) Appl. No.: 12/527,345

(22) PCT Filed: Feb. 4, 2008

(86) PCT No.: PCT/CN2008/000318
§ 371 (c)(1),
(2), (4) Date: Feb. 5, 2010

(87) PCT Pub. No.: WO2008/098485
PCT Pub. Date: Aug. 21, 2008

(65) Prior Publication Data
US 2010/0168142 A1    Jul. 1, 2010

(30) Foreign Application Priority Data
Feb. 14, 2007    (CN) .......................... 2007 1 0037557

(51) Int. Cl.
*A61K 31/517*    (2006.01)
(52) U.S. Cl. ..................... 514/266.4; 544/293
(58) Field of Classification Search .................. 544/293
See application file for complete search history.

(56) References Cited

FOREIGN PATENT DOCUMENTS

| EP | 0520722 | 12/1992 |
|---|---|---|
| EP | 0566226 | 10/1993 |
| EP | 0635498 | 1/1995 |
| EP | 1990337 A1 | 11/2008 |
| WO | WO96/30347 | 10/1996 |
| WO | WO97/38983 | 10/1997 |
| WO | WO99/35146 | 7/1999 |
| WO | WO00/06555 | 2/2000 |
| WO | WO 02/02552 * | 1/2002 |
| WO | WO2006/071017 | 7/2006 |
| WO | WO2007/082434 | 7/2007 |

OTHER PUBLICATIONS

International Search Report and Written Opinion for PCT application No. PCT/CN2008/000318, date of mailing Mar. 27, 2008.
Wissner et al. "Syntheses and EGFR kinase inhibitory activity of 6-substituted-4-anilino [1,7] and [1,8] naphthyridine-3-carbonitriles", *Bioorganic & Medicinal Chemistry Letters* 14(6):1411-1416 (2004).
Zhang et al. "Synthesis and SAR of potent EGFT/erbB2 dual inhibitors", *Bioorganic & Medicinal Chemistry Letters* 14:111-114 (2004).
Supplementary European Search Report corresponding to European Application No. 08706496.0 dated Mar. 23, 2010.

* cited by examiner

*Primary Examiner* — Brian McDowell
(74) *Attorney, Agent, or Firm* — Myers Bigel Sibley & Sajovec, PA

(57) ABSTRACT

The present invention relates to salt forms of N-{4-[3-chloro-4-(3-fluoro-benzyloxy)phenylamino]-quinazolin-6-yl}-acrylamide as exemplified by formula (I), methods of preparation thereof, pharmaceutical compositions comprising the same and their use thereof. The salt forms of the present invention, which possess excellent tumor inhibitory activity, good bioavailability and low toxicity in an animal body, are suitable for use of preparation of anti-tumor medicaments.

(I)

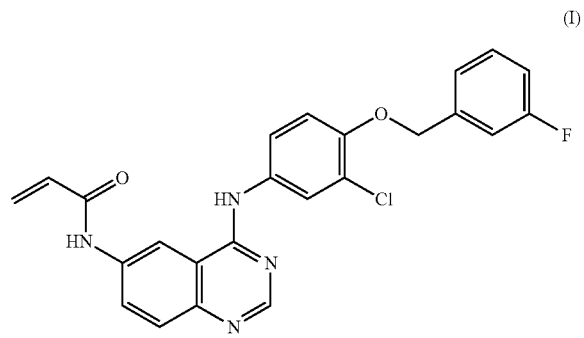

22 Claims, No Drawings

US 8,349,854 B2

SALTS OF 4-ANILINE QUINAZOLINE DERIVATIVE

CROSS REFERENCE TO RELATED APPLICATIONS

This application is a 35 U.S.C. §371 national phase application of PCT Application No. PCT/CN2008/000318, filed on Feb. 4, 2008, which claims priority from Chinese Patent Application 200710037557.2, filed on Feb. 14, 2007, the disclosures and contents of which are incorporated by reference herein in their entirety. The above-referenced PCT International Application was published in Chinese as International Publication No. WO2008/098485.

FIELD OF THE INVENTION

The present invention relates to the salts of 4-phenylamino quinazoline derivatives. Specifically, the present invention relates to the salt forms of N-{4-[3-chloro-4-(3-fluoro-benzyloxy)phenylamino]-quinazolin-6-yl}-acrylamide, methods for preparation thereof, pharmaceutical compositions comprising the same and their use in prevention and/or treatment of tumors.

BACKGROUND OF THE INVENTION

Cancer is recognized as one of the diseases mediated by the signal transduction system or signal transduction mechanism in cell. The proliferation of cell is directed by many extracellular orders received by the cell. The aim of the signal transduction system is to receive these or other signals from the surface of the cell, and to introduce them into the cell. Then these signals are transmitted into nucleolus and skeleton of the cell, which affect the transcription of gene and the synthesis of protein.

The most common pathogenesis of cancer is a series of defects. Said defects can be the defects of some proteins (when mutation occurs), or the lack of regulation of the amount of proteins in cell, which results in excessive or deficient production of some proteins. Generally, the constitutive state can be induced by the serious injury in cell, and hence the signal for proliferation is received by the nucleus while these signals do not exist in fact. The occurrence of such case may result from many mechanisms. Sometimes, some corresponding growth factors of their autoreceptors are produced by cell in an inappropriate way, which is the so called autocrine loop mechanism.

There are many receptors existing on the cell surface. The interaction between growth factors and these receptors is required for the normal regulation of cell growth. However, in some case, the mutation or overexpression of any of these receptors will result in abnormal receptors and hence the uncontrolled proliferation of the cell, which may result in tumor cells and cancer in the end.

Epidermal growth factors receptors (EGFR) are identified as a significant driving factor in the growth and proliferation process of cell. In common tumors, such as non-small cell lung cancer, epidermal growth factors receptors are expressed excessively, which is far beyond the normal range. The epidermal growth factors receptor family consists of EGFR (Erb-B1), Erb-B2 (HER-2/neu), Erb-B3 and Erb-B4. The epidermal growth factors receptors are related to the progression of most cancers, especially colonic cancer and mammary cancer. The overexpression of said receptors has been confirmed as the primary risk factor for a poor-prognosis mammary cancer. Besides, it has been confirmed that all of the above four members of the receptor family can polymerize with other member of the family to form a heterodimer, forming the signal transduction complex. The overexpression of more than one member of said family in malignant cells will result in the cooperation of the signal transduction.

EGFR belongs to the protein tyrosine kinase (PTK) family. The protein tyrosine kinase is an enzyme which catalyzes the transportation of phosphate groups from ATP to tyrosine residues located on the protein substrate. Protein tyrosine kinases play important roles in normal cell growth. The overexpression of EGFR may cause the activation of receptors without ligands and the phosphorylation of certain protein, and then the fissional signal is given. As a result, EGFR may magnify the weak signal excessively by the auto-tyrosine-kinases action, which results in excessive cell proliferation.

Due to the important effect of the abnormal receptor tyrosine kinases on the pathogenesis of cancer, many of the recent researches relate to specific PTK inhibitors as potential anti-cancer drugs. European patent application EP520722A1 discloses some 4-phenylamino-phthalazinone derivatives with PTK inhibitory activity. European patent application EP566226A1 discloses some 4-phenylamino-phthalazinone derivatives with a plurality of substituents at positions 5 to 8 thereof having PTK inhibitory activity. European patent application EP635498A1 discloses some 4-phenylamino-phthalazinone derivatives having PTK inhibitory activity, which must contain one halogen substituent at position 7 and a plurality of substituents at position 6.

WO 96/30347 (Chinese patent application CN 96102992) relates to a series of 4-(substituted-phenylamino)-quinazoline derivatives, their prodrug, their pharmaceutically acceptable salts and their uses in treating diseases induced by over proliferation.

WO 97/38983 (Chinese patent application CN 97194458) provides the compounds as irreversible inhibitor of tyrosine kinases.

WO 99/35146 (Chinese patent application CN 99803887) discloses bicyclic heteroaromatic compounds as protein tyrosine kinase inhibitors.

WO 00/06555 (Chinese patent application CN 99808949) also relates to substituted quinazoline derivatives having PTK inhibitory activity.

WO 2006/071017 also mentions some quinazoline derivatives that inhibit growth of cancer cells.

PCT/CN2006/002786, filed by the applicant of the present invention on Oct. 20, 2006, describes a novel type of 4-phenylamino quinazoline derivatives and their uses as PTK inhibitors, wherein, it is proven by experiments that the compound N-{4-[3-chloro-4-(3-fluoro-benzyloxy)phenylamino]-quinazolin-6-yl}-acrylamide obtained in Example 8 possesses relatively good inhibitory activity of human epidermoid squamous cancer cells A431 and human mammary cancer cells BT-474. The compound also possesses conspicuous anti-tumor effect on human epidermoid squamous cancer cells A431 transplanted to a nude rat. It is also proven in vitro that the compound has excellent inhibitory activity against Erb-B2. The contents of the document are hereby incorporated in their entireties by reference herein.

CONTENTS OF THE INVENTION

The technical problem to be solved by the present invention is to provide novel salt forms of N-{4-[3-chloro-4-(3-fluoro-benzyloxy)phenylamino]-quinazolin-6-yl}-acrylamide (as defined in formula (I)), methods for preparation thereof, pharmaceutical compositions comprising the same and their use in prevention and/or treatment of tumors. The salt forms of the present invention, which possess excellent tumor inhibitory activity, good bioavailability and low toxicity in an animal body, are suitable for the preparation of the formulations of anti-tumor medicaments.

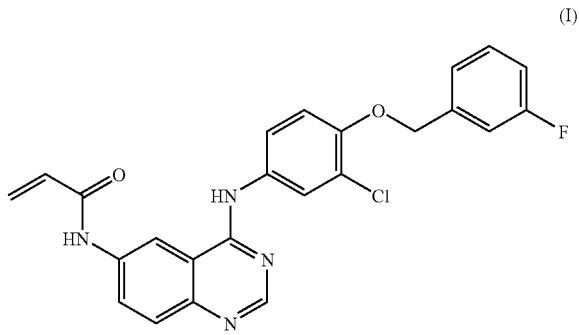 [SMILES: C=CC(=O)Nc1ccc2ncnc(Nc3ccc(OCc4cccc(F)c4)c(Cl)c3)c2c1]

(I)

In accordance with the first aspect of the present invention there is provided a pharmaceutically acceptable salt of compound of formula (I). The term "pharmaceutically acceptable salt", as used herein, refers to an acid addition salt or a base addition salt which is comparatively pharmaceutically innoxious. Said acid addition salt is formed from the compound of formula (I) with a suitable inorganic acid or organic acid, including, such as, hydrobromide, hydrochloride, sulfate, bisulfate, carbonate, bicarbonate, sulfite, phosphate, biphosphate, acetate, oxalate, malonate, valerate, oleate, palmitate, stearate, laurate, borate, p-toluenesulfonate, methanesulfonate, tartrate, benzoate, lactate, toluate, citrate, maleate, fumarate, malate, pamoate, salicylate, vanillate, mandelate, succinate, gluconate, lactobionate, lauryl sulfonate and the like. Said base addition salt is formed from the compound of formula (I) with a suitable inorganic or organic base, including, for example, the salts formed by the compound of formula (I) with an alkali metal, alkali earth metal, quaternary ammonium cation, such as sodium salts, lithium salts, potassium salts, calcium salts, magnesium salts, tetramethyl quaternary ammonium salts, tetraethyl quaternary ammonium salts and the like; amine salts, including the salts formed by the compound of formula (I) with ammonia ($NH_3$), primary amines, secondary amines or tertiary amines, such as methyl amine salt, dimethyl amine salt, trimethylamine salt, triethylamine salt, ethylamine salt and the like, especially triethylamine salt.

In a preferred embodiment of the present invention, said salt is acid addition salts, including inorganic acid addition salts and organic acid addition salts, wherein the inorganic acid addition salt can be selected from hydrobromide, hydrochloride, sulfate, carbonate, sulfite, phosphate or borate. The organic acid addition salt can be selected from acetate, oxalate, malonate, valerate, p-toluenesulfonate, methanesulfonate, tartrate, benzoate, lactate, toluate, citrate, maleate, fumarate, malate, pamoate, salicylate, vanillate, mandelate or succinate. Further preferred acid addition salts are hydrochloride, sulfate, phosphate, carbonate, p-toluenesulfonate, methanesulfonate, benzoate, salicylate, oxalate, acetate, valerate, malonate or tartrate, especially hydrochloride, sulfate, p-toluenesulfonate, methanesulfonate, oxalate or tartrate.

In the most preferred embodiment of the present invention, said salt is hydrochloride or p-toluenesulfonate.

In accordance with the second aspect of the present invention there is provided a process for preparing the pharmaceutically acceptable salt of the present invention, wherein said salt is obtained by treating N-{4-[3-chloro-4-(3-fluoro-benzyloxy)phenyl amino]-quinazolin-6-yl}-acrylamide with a suitable acid or base, comprising the following steps:

(a) dissolving N-{4-[3-chloro-4-(3-fluoro-benzyloxy)phenylamino]-quinazolin-6-yl}-acrylamide in a suitable organic solvent, and adding thereto the solution containing the relevant acid or the relevant base with stir;

(b) filtering the resulting mixture directly or after concentrating to obtain a solid; water-washing, and drying the solid to obtain the desired salt.

The organic solvent, can be selected, for example, from methanol, ethanol, ethyl acetate, tetrahydrofuran, triethylamine, diethyl ether, 1,4-dioxane or a mixture thereof. The acid includes inorganic acids such as hydrobromic acid, hydrochloric acid, sulfuric acid, carbonic acid, sulfurous acid, phosphorous acid and boric acid, and organic acids such as acetic acid, oxalic acid, malonic acid, valeric acid, oleic acid, palmitic acid, stearic acid, lauryl acid, p-toluenesulfonic acid, methanesulfonic acid, tartaric acid, benzoic acid, lactic acid, toluic acid, citric acid, maleic acid, fumaric acid, malic acid, pamoic acid, salicylic acid, vanillic acid, mandelic acid, succinic acid, gluconic acid, lactobionic acid, lauryl sulfonic acid and the like. The base includes inorganic and organic bases, such as hydroxide or carbonate of an alkali metal, alkali earth metal or quaternary ammonium, ammonia, methylamine, dimethylamine, trimethylamine, triethylamine, ethylenediamine and the like.

Usually, the above-mentioned process may be conducted under cooled condition, at room temperature or under heated condition. It is noticeable that the selection of the reaction temperature can have certain influence on different salt-forming reactions, which is also known by the person skilled in the art. The temperature of the salt-forming reaction according to the present invention ranges from −10° to the boiling point of the solvent used, and preferably 0° C.~40° C. The person skilled in the art can easily determine the most preferred reaction temperature of specific salt-forming reaction by the conventional means in the art.

In one embodiment, the present invention provides the process for preparing the preferred hydrochloride according to the invention, comprising:

(a) dissolving N-{4-[3-chloro-4-(3-fluoro-benzyloxy)phenylamino]-quinazolin-6-yl}-acrylamide in the mixture of ethyl acetate and triethylamine or the mixture of tetrahydrofuran and triethylamine, and adding dropwise thereto the solution of HCl in 1,4-dioxane slowly with stir, and causing solid being precipitated from the mixture;

(b) stopping the stir, collecting the solid by filtration, water-washing and drying the solid to obtain the hydrochloride of N-{4-[3-chloro-4-(3-fluoro-benzyloxy)phenyl-amino]-quinazolin-6-yl}-acrylamide.

In another embodiment, the present invention provides the process for preparing the preferred p-toluenesulfonate according to the invention, comprising:

(a) dissolving N-{4-[3-chloro-4-(3-fluoro-benzyloxy)phenylamino]-quinazolin-6-yl}-acrylamide in the mixture of methanol and tetrahydrofuran, adding dropwise thereto the solution of p-toluenesulfonic acid in the mixture of methanol and tetrahydrofuran slowly with stir, and causing solid being precipitated from the mixture;

(b) stopping the stir, collecting the solid by filtration, water-washing and drying the solid to obtain the p-toluenesulfonate of N-{4-[3-chloro-4-(3-fluoro-benzyloxy)phenylamino]-quinazolin-6-yl}-acrylamide.

In addition, the acid addition salt of N-{4-[3-chloro-4-(3-fluoro-benzyloxy)phenylamino]-quinazolin-6-yl}-acrylamide can also be prepared by other known methods for preparing an acid addition salt of amine in the art.

In accordance with the third aspect of the present invention there is provided a pharmaceutical composition comprising the salt according the invention and pharmaceutically acceptable carries.

The pharmaceutical composition may be administered to mammalian (e.g., human) by oral, rectal, parenteral (e.g., intravenous, intramuscular or subcutaneous), or topical route. When the pharmaceutical composition is used, an effective amount for treatment or prevention of the salt of the present invention is administered to mammalian (e.g., human) which needs such treatment or prevention. The term "an effective amount for treatment or prevention" refers to an amount of the active compound sufficient to cause the biological or medical response in mammalian (e.g., human) sought by the veterinarian or clinical physician. Ordinary physician, veterinarian and clinical physician can easily determine the effective amount of the salt of the present invention for the treatment or prevention of the designated diseases, which is usually 0.01~20 mg/kg of body weight/per day, and preferably 0.1~10 mg/kg of body weight/per day. More specifically, the daily dosage for a person of a body weight of 60 kg is usually 1~1000 mg, and preferably 20~500 mg. It is certain that the specific dosage will depend upon a number of factors such as the age, gender, weight and general health as well as the precise condition requiring treatment of the patient being treated, all of which are well within the abilities of the skilled physician. The term "mammalian" used herein includes but is not limited to cat, dog, rabbit, goat, sheep, mouse, rat, human and the like. Human is particularly preferred.

The pharmaceutical compositions can be formulated in solid dosage forms for oral administration, including capsules, tablets, pills, powders, granules, dragees and the like. In such solid dosage forms, the salt of the present invention can be mixed with at least one inert excipient (or carrier). The inert excipient (or carrier) includes but is not limited to (a) fillers or extenders, such as starch, lactose, sucrose, glucose, mannitol and silicic acid; (b) binders, such as hydroxymethyl cellulose, alginate, gelatin, polyvinylpyrrolidone, sucrose or acacia; (c) humectants, such as glycerol; (d) disintegrants, such as agar, calcium carbonate, potato starch or cassava starch, alginic acid, some composite silicates, polyvinylpyrrolidone and sodium carbonate; (e) retarding solvents, such as paraffin; (f) absorption accelerators, such as quaternary ammonium compounds; (g) wetting agents, such as cetyl alcohol and glycerol monostearate; (h) adsorbents, such as kaolin; and (i) lubricants, such as talc, calcium stearate, magnesium stearate, solid polyethylene glycol, sodium dodecyl sulfate or the mixtures thereof. Capsules, tablets and pills can also contain buffers.

The solid dosage forms such as tablets, dragees, capsules, pills or granulas can be prepared with coating and shell materials, such as enteric coatings or other materials well known in the art, which may contain opacifier. Besides, the release of the active compound in the composition can be a partial release at some part of the alimentary canal in a delayed manner. When necessary, the active compound can be formulated in microencapsulated form with one or more of the above excipients.

The pharmaceutical composition can also be formulated in a liquid dosage form for oral administration, including pharmaceutically acceptable emulsion, solution, suspension, syrup or tincture. Except for the salt of the present invention as an active compound, the liquid dosage form may also contain inert diluents commonly used in the art, such as water or other solvents, solubilizers and emulsifiers, such as ethanol, isopropanol, ethyl carbonate, ethyl acetate, propanediol, 1,3-butanediol, dimethylformamide and oils, in particular, cottonseed oil, peanut oil, corn germ oil, olive oil, castor oil and sesame oil, or the mixtures thereof. Except for these inert diluents, the composition can also comprise auxiliaries, such as wetting agents, emulsifiers and suspending agents, sweeteners, flavoring agents and perfuming agents.

When the salt of the present invention is formulated in a suspension, the suspension may further comprise suspending agents, such as ethoxylated isooctadecanol, polyoxyethylene sorbitol, and sorbitan ester, microcrystalline cellulose, aluminium methoxide and agar, or the mixtures thereof, and the like.

The pharmaceutical compositions can be formulated in a dosage form for parenteral injection, including physiologically acceptable sterile aqueous or nonaqueous solution, dispersion, suspension or emulsion, and sterile powder which can be reconstructed to form sterile injectable solution or dispersion. Aqueous and nonaqueous carriers, diluents, solvents or excipients can be used to prepare the sterile aqueous and nonaqueous solution, dispersion, suspension or emulsion. Suitable aqueous and nonaqueous carriers, diluents, solvents or excipients include water, ethanol, polyol and suitable mixtures thereof.

The pharmaceutical compositions can be formulated in a dosage form for topical administration, including ointment, cream, powder, patch, spray and inhalant. The salt of the present invention can be mixed with physiologically acceptable carriers and any antiseptics, buffers, or required propellants, if necessary, under sterile condition.

In another aspect, the salt of the present invention can be used in the preparation of medicaments for the treatment or prevention of diseases mediated by protein tyrosine kinases. Said diseases include tumors, especially malignant tumors, such as breast cancer, non-small cell lung cancer, ovarian cancer, gastric cancer, colonic cancer, pancreatic cancer, epidermoid squamous cancer and the like.

In accordance with a further aspect of the present invention there is also provided the method for the treatment and/or prevention of tumors in mammalian, comprising administering an effective amount for treatment or prevention of the salt of the present invention to the mammalian which needs such treatment or prevention.

The salt of the present invention may be administered alone or in combination with other pharmaceutically acceptable therapeutic agents, especially with other anti-tumor drugs. The therapeutic agents include but are not limited to anti-tumor drugs which exert an influence on the chemical structure of DNA, such as Cisplatin, anti-tumor drugs such as Methotrexate (MIX), 5-Fluorouracil (5FU) and the like which affect the synthesis of nucleic acid, anti-tumor drugs such as Adriamycin, Epirubicin, Aclacinomycin, Mitramycin and the like which affect the transcription of nucleic acid, anti-tumor drugs such as Paclitaxel, Vinorelbine and the like which exert an influence on synthesis of tubulin, aromatase inhibitors such as Aminoglutethimide, Lentaron, Letrozole, Anastrozole and the like, inhibitors of the cell signal pathway such as Imatinib, Gefitinib, Erlotinib, and the like. Each therapeutic agent to be combined can be administered simultaneously or sequentially, and can be administered either in a unitary formulation or in separate formulations. Such combination includes not only the combination of the salt of the present invention with another active ingredient but also the combination of the salt of the present invention with two or more other active ingredients.

The main advantages of the present invention include:

(a) It is proved by the experiments in vivo that the salts of the present invention possess excellent bioavailability;

(b) It is proved by the experiments that the salts of the present invention possess excellent anti-tumor activity;

(c) It is proven by the experiments in vivo that the salts of the present invention possess low toxicity and a high safety profile.

The present invention will now be described in connection with certain embodiments which are not intended to limit its scope. It should be recognized thus that the following examples are for the purposes of illustration of the practice of the present invention only. The specific condition of the experimental methods used in the following examples, which was not set forth, is generally according to the conventional condition, or according to the condition suggested by the manufacturers. The materials used are obtained commercially or could be easily obtained according to the known literature methods by the person skilled in the art. As used herein, the abbreviation THF represents tetrahydrofuran, EA represents ethyl acetate, DMSO represents dimethyl sulfoxide, PVPP represents polyvinylpolypyrrolidone, PVP represents polyvinylpyrrolidone, ig refers to intragastric administration, and iv refers to intravenous injection. Unless otherwise indicated, the amounts and percents are measured by weight.

EXAMPLES

Example 1

N-{4-[3-chloro-4-(3-fluoro-benzyloxy)phenylamino] quinazolin-6-yl}-acrylamide

Step A: The preparation of 4-[3-chloro-4-(3-fluoro-benzyloxy)phenylamino]-6-nitro-quinazoline 1) 2.85 g (15 mmol) of 6-nitro-quinazolone and 25 ml of phosphorus oxychloride were added to a flask of 100 ml equipped with a reflux condenser and then refluxed for 3 hours at 105° C., which was then poured carefully into ice-water system of 150 ml. The squamose solid precipitated slowly. The solid was collected by filtration and dried, and was then identified as 4-chloro-6-nitro-quinazoline with a yield of 78%.

$^1$H-NMR (400 MHz, CDCl$_3$): δ9.22 (2H, s), 8.74 (1H, dd, J=2.57 Hz, 9.16 Hz), 8.27 (1H, d, J=9.16 Hz).

2) 4.65 g (26.6 mmol) of 2-chloro-4-nitrophenol, 3.31 ml (27.0 mmol, 1 eq) of m-fluorobenzyl bromide, 9.4 g (54 mmol, 2 eq) of potassium carbonate and 50 ml of dimethyl formamide were added to a flask of 250 ml equipped with a reflux condenser, and then heated and refluxed. The solid was removed by filtration while it was still warm after 4 hours of reaction. The filtrate was cooled to room temperature, diluted with 300 ml of ethyl acetate, and washed with water for three times. The organic phase was dried, concentrated and purified by column chromatography to obtain a solid product. Said solid product was placed in a flask of 250 ml equipped with a refluxing condenser and 4.7 g (87 mmol) of Fe powders, 10 ml of glacial acetic acid and 50 ml of absolute ethyl alcohol were added thereto. The resulting mixture was heated and refluxed for 5 hours, cooled to the room temperature, and then extracted with a large amount of the mixed solvent of water-ethyl acetate. The organic phases were combined; washed with the sodium bicarbonate solution for twice, dried, concentrated and purified by column chromatography to obtain a light brown solid with a yield of 75%, which was identified as 4-(3-fluorobenzyloxy)-3-chloroaniline.

$^1$H-NMR (400 MHz, CDCl$_3$): δ7.38-7.29 (1H, m), 7.23-7.16 (2H, m), 7.04-6.96 (1H, m), 6.79-6.74 (2H, m), 6.50 (1H, dd. J=2.75 Hz, 8.61 Hz), 5.03 (2H, s), 3.50 (2H, br).

3) 1.20 g (5.7 mmol) of 4-chloro-6-nitro-quinazoline and 1.37 g (5.6 mmol) of 4-(3-fluoro-benzyloxy)-3-chloro-aniline were dissolved in 80 mL of isopropanol and refluxed for 3 hours. A large amount of yellow solid precipitated from the system. The solid was collected by filtration, washed with saturated sodium bicarbonate solution till pH=8 and dried under vacuum to obtain 1.62 g (3.75 mmol) of yellow solid, which was identified as the compound 4-[3-chloro-4-(3-fluoro-benzyloxy)phenylamino]-6-nitro-quinazoline with a yield of 67%.

$^1$H-NMR (400 MHz, CDCl$_3$): δ11.30 (1H, br), 9.54-9.48 (1H, m), 8.45-8.41 (1H, m), 8.31-8.25 (1H, m), 7.98-7.89 (1H, m), 7.50-7.47 (1H, m), 7.35-7.26 (1H, m), 7.05-6.96 (1H, m), 6.90-6.80 (2H, m), 7.74-7.60 (2H, m), 4.84 (2H, s).

Step B: The preparation of 4-[3-chloro-4-(3-fluoro-benzyloxy)phenylamino]-6-amino-quinazoline 1.60 g (3.77 mmol) of compound 4-[3-chloro-4-(3-fluoro-benzyloxy)phenyl-amino]-6-nitro-quinazoline prepared according to the method of Step A, 1.05 g (18.85 mmol, 5 eq) of Fe powders, 2 mL of glacial acetic acid and 40 mL of methanol were added to a flask equipped with a refluxing condenser and refluxed for 2.5 hours in a 85° oil-bath. The Fe powders were removed by filtration. The filtrate was diluted with ethyl acetate and washed sequentially with sodium bicarbonate solution and water. The organic phase was dried and concentrated to obtain 900 mg (2.28 mmol) of yellow powder. Said compound was identified as 4-[3-chloro-4-(3-fluoro-benzyloxy)phenyl-amino]-6-amino-quinazoline with a yield of 61%.

$^1$H-NMR (400 MHz, DMSO): δ9.32 (1H, s), 8.31 (1H, s), 8.04 (1H, d. J=2.64 Hz), 7.73 (1H, dd, J=2.64 Hz, 8.80 Hz), 7.54-7.43 (2H, m), 7.36-7.28 (3H, m), 7.26-7.14 (3H, m), 5.57 (2H, br), 5.27 (2H, s).

Step C: The preparation of N-{4-[3-chloro-4-(3-fluoro-benzyloxy)phenylamino]-quinazolin-6-yl}-acrylamide 1.2 g (3.04 mmol) of the compound 4-[3-chloro-4-(3-fluoro-benzyloxy)phenyl-amino]-6-amino-quinazoline obtained according to Step B, 0.6 mL (4.58 mmol, 1.5 eq) of triethylamine, 0.28 mL (3.33 mmol, 1.1 eq) of acrylic chloride and 40 mL of THF were added to a flask in an ice-bath. The temperature rose to room temperature slowly. The reaction was stopped after 3 hours, The solid was collected by filtration and washed with water to neutral and dried to obtain 1.0 g (2.23 mmol) of yellow solid, which was identified as N-{4-[3-chloro-4-(3-fluoro-benzyloxy)phenylamino]-quinazolin-6-yl}-acrylamide with a yield of 67%. MS: 449. mp: 222-225°.

$^1$H-NMR (400 MHz, CDCl$_3$+DMSO): δ8.75 (1H, s), 8.60-8.52 (2H, m), 7.81 (1H, d, J=2.44 Hz), 7.69 (2H, s), 7.54 (1H, dd, J=2.56 Hz, 8.92 Hz), 7.30-7.22 (2H, m), 7.18-7.08 (2H, m), 6.96-6.86 (2H, m), 6.37 (2H, d, J=5.86 Hz), 5.67 (1H, t, J=5.86 Hz), 5.06 (2H, s).

Example 2

The hydrochloride of N-{4-[3-chloro-4-(3-fluoro-benzyloxy)phenyl-amino]-quinazolin-6-yl}-acrylamide 1.0 g (2.23 mmol) of the compound N-{4-[3-chloro-4-(3-fluoro-benzyloxy)phenyl-amino]-quinazolin-6-yl}-acrylamide prepared according to Example 1 was dissolved in 20 mL of the mixture of ethyl acetate and triethylamine (EA/Et$_3$N=40/1). The solution was stirred in an ice-water bath and thereto, 2 mL of the solution of HCl in 1,4-dioxane (4 mol/L) was added dropwise slowly. Some yellow solid precipitated, and the stir was stopped after 45 min. The solid was collected by filtration, washed with water and dried to obtain 530 mg (1.09 mmol) of Kelly solid, which was identified as the hydrochloride of N-{4-[3-chloro-4-(3-fluoro-benzyloxy)phenylamino]-quinazolin-6-yl}-acryl amide with a yield of 49%. MS: 449. mp: 249-252°.

$^1$H-NMR (400 MHz, CDCl$_3$+DMSO): δ8.91 (1H, s), 8.76-8.69 (2H, m), 8.01 (1H, d), 7.83 (2H, s), 7.68 (1H, dd), 7.46-7.33 (2H, m), 7.34-7.29 (2H, m), 7.23-7.18 (2H, m), 6.51 (2H, d), 6.28 (1H, t), 5.61 (2H, s).

The desired hydrochloride of N-{4-[3-chloro-4-(3-fluoro-benzyloxy)phenyl-amino]-quinazolin-6-yl}-acrylamide can also be prepared by the following process: 1.0 g (2.23 mmol) of N-{4-[3-chloro-4-(3-fluoro-benzyloxy)phenylamino]-quinazolin-6-yl}-acrylamide was dissolved in 20 ml of the mixture of tetrahydrofuran and triethylamine (THF/Et$_3$N=40/1). The solution was stirred in an ice-water bath, and thereto, 2 mL of the solution of concentrated HCl in 1,4-dioxane (4N) was added dropwise slowly. Some yellow solid precipitated, and the stir was stopped after 45 min. The solid was collected by filtration, washed with water and dried to obtain 370 mg (0.76 mmol) of the hydrochloride of N-{4-[3-chloro-4-(3-fluoro-benzyloxy)phenylamino]-quinazolin-6-yl}-acrylamide with a yield of 34%.

Example 3

The sulfate of N-{4-[3-chloro-4-(3-fluoro-benzyloxy)phenylamino]-quinazolin-6-yl}-acrylamide According to the method described in Example 2, the solution of sulfuric acid in 1,4-dioxone (2 mol/L) was used instead of the solution of HCl in 1,4-dioxane (4 mol/L). The sulfate of N-{4-[3-chloro-4-(3-fluoro-benzyloxy)phenylamino]-quinazolin-6-yl}-acrylamide was obtained.

$^1$H-NMR (400 MHz, CDCl$_3$+DMSO): δ8.99 (1H, s), 8.82-8.76 (2H, m), 8.10 (1H, d), 7.90 (2H, s), 7.74 (1H, dd), 7.53-7.40 (2H, m), 7.42-7.37 (2H, m), 7.31-7.26 (2H, m), 6.60 (2H, d), 6.35 (1H, t), 5.70 (2H, s).

Example 4

The phosphate of N-{4-[3-chloro-4-(3-fluoro-benzyloxy)phenylamino]-quinazolin-6-yl}-acrylamide According to the method described in Example 2, the solution of phosphoric acid in 1,4-dioxone (2 mol/L) was used instead of the solution of HCl in 1,4-dioxane (4 mol/L). The phosphate of N-{4-[3-chloro-4-(3-fluoro-benzyloxy)phenylamino]-quinazolin-6-yl}-acrylamide was obtained.

$^1$H-NMR (400 MHz, CDCl$_3$+DMSO): δ8.95 (1H, s), 8.78-8.72 (2H, m), 8.07 (1H, d), 7.86 (2H, s), 7.70 (1H, dd), 7.50-7.36 (2H, m), 7.38-7.33 (2H, m), 7.27-7.22 (2H, m), 6.56 (2H, d), 6.30 (1H, t), 5.64 (2H, s).

Example 5

The carbonate of N-{4-[3-chloro-4-(3-fluoro-benzyloxy)phenylamino]-quinazolin-6-yl}-acrylamide According to the method described in Example 2, the solution of carbonic acid in 1,4-dioxone (2 mol/L) was used instead of the solution of HCl in 1,4-dioxane (4 mol/L). The carbonate of N-{4-[3-chloro-4-(3-fluoro-benzyloxy)phenylamino]-quinazolin-6-yl}-acrylamide was obtained.

$^1$H-NMR (400 MHz, CDCl$_3$+DMSO): δ8.97 (1H, s), 8.90-8.74 (2H, m), 8.09 (114, d), 7.87 (2H, s), 7.72 (1H, dd), 7.52-7.38 (2H, m), 7.40-7.35 (2H, m), 7.29-7.24 (2H, m), 6.58 (2H, d), 6.32 (1H, t), 5.66 (2H, s).

Example 6 p-Toluenesulfonate of N-{4-[3-chloro-4-(3-fluoro-benzyloxy)phenylamino]quinazolin-6-yl}-acrylamide 3 g (6.68 mmol) of the compound N-{4-[3-chloro-4-(3-fluoro-benzyloxy)phenyl-amino]-quinazolin-6-yl}-acrylamide prepared according to Example 1 was dissolved in the mixture of tetrahydrofuran and methanol (THF/CH$_3$OH=1/1), and the solution of p-toluenesulfonic acid (6 eq, 7.62 g) in the mixture of methanol and tetrahydrofuran (THF/CH$_3$OH=1/1, 24 mL) was added dropwise into the system slowly, and then a large amount of yellow solid precipitated from the system. The solid was collected by filtration, washed with water and dried under vacuum to obtain 2.93 mg (4.72 mmol) of Kelly solids, which was identified as the p-toluenesulfonate of N-{4-[3-chloro-4-(3-fluoro-benzyloxy)phenylamino]-quinazolin-6-yl}-acrylamide with a yield of 70%.

Elementary analysis (C$_{31}$H$_{26}$ClFN$_4$O$_5$S):

Calculated value: C, 59.95%; H, 4.22%; N, 9.02%; S, 5.16%.

Measured value: C, 60.01%; H, 4.22%; N, 8.99%; S, 5.13%.

$^1$H-NMR (400 MHz, CDCl$_3$+DMSO): δ10.78 (1H, s) 9.07 (1H, s), 8.89 (1H, s), 8.06-8.04 (1H, d), 7.88-7.84 (2H, t), 7.59-7.57 (1H, d), 7.50-7.44 (3H, dd), 7.35-7.30 (3H, m), 7.21-7.16 (1H, t), 7.10-7.08 (2H, d), 6.54-6.48 (1H, dd), 6.38-6.34 (1H, d), 5.90-5.87 (2H, d), 2.26 (3H, s).

The desired p-toluenesulfonate of N-{4-[3-chloro-4-(3-fluoro-benzyloxy)phenyl-amino]-quinazolin-6-yl}-acrylamide can also be prepared according to the following process: 3 g (6.68 mmol) of N-{4-[3-chloro-4-(3-fluoro-benzyloxy)phenylamino]-quinazolin-6-yl}-acrylamide was dissolved in the mixture of tetrahydrofuran and methanol (THF/CH$_3$OH=2/1, 30 mL). The solution of p-toluenesulfonic acid (1 eq, 1.27 g) in the mixture of methanol and tetrahydrofuran (THF/CH$_3$OH=1/1, 24 mL) was added dropwise to the system slowly, and a large amount of yellow solid precipitated from the system afterwards. The solid was collected by filtration, washed with water and dried under vacuum to obtain 2.6 g (4.19 mmol) of the p-toluenesulfonate of N-{4-[3-chloro-4-(3-fluoro-benzyloxy)phenylamino]-quinazolin-6-yl}-acrylamide with a yield of 63%.

Example 7

Methanesulfonate of N-{4-[3-chloro-4-(3-fluoro-benzyloxy)phenylamino]-quinazolin-6-yl}-acrylamide According to the method described in Example 6, the methanesulfonic acid (6 eq, 4.25 g) was used instead of p-toluenesulfonic acid. The methanesulfonate of N-{4-[3-chloro-4-(3-fluoro-benzyloxy)phenylamino]-quinazolin-6-yl}-acrylamide was obtained.

$^1$H-NMR (400 MHz, CDCl$_3$+DMSO): δ9.05 (1H, s), 8.95-8.79 (2H, m), 8.15 (1H, d), 7.93 (2H, s), 7.77 (1H, dd), 7.57-7.43 (2H, m), 7.45-7.40 (2H, m), 7.34-7.29 (2H μm), 6.63 (2H, d), 6.37 (1H, t), 5.71 (2H, s), 2.87 (3H, s).

Example 8

Benzoate of N-{4-[3-chloro-4-(3-fluoro-benzyloxy) phenylamino]-quinazolin-6-yl}-acrylamide According to the method described in Example 6, the benzoic acid (6 eq, 4.76 g) was used instead of p-toluenesulfonic acid. The benzoate of N-{4-[3-chloro-4-(3-fluoro-benzyloxy)phenylamino]-quinazolin-6-yl}-acrylamide was obtained.

$^1$H-NMR (400 MHz, CDCl$_3$+DMSO): δ10.70 (1H, s), 8.98 (1H, s), 8.80 (114, s), 7.08-7.00 (1H, d), 7.81-7.76 (2H, t), 7.51-7.49 (114, d), 7.42-7.36 (3H, dd), 7.27-7.22 (3H, m), 7.14-7.08 (1H, t), 7.02-7.00 (2H, d), 6.48-6.40 (1H, dd,), 6.30-6.26 (1H, d), 5.82-5.80 (214, d), 2.40 (3H, s).

Example 9

Salicylate of N-{4-[3-chloro-4-(3-fluoro-benzyloxy) phenylamino]-quinazolin-6-yl}-acrylamide According to the method described in Example 6, the salicylic acid (6 eq, 5.39 g) was used instead of p-toluenesulfonic acid. The salicylate of N-{4-[3-chloro-4-(3-fluoro-benzyloxy)phenylamino]-quinazolin-6-yl}-acrylamide was obtained.

Elementary analysis (C$_{31}$H$_{24}$ClFN$_4$O$_5$):
Calculated value: C, 64.43%; H, 4.12%; N, 9.54%.
Measured value: C, 64.48%; H, 4.12%; N, 9.52%.

$^1$H-NMR (400 MHz, CDCl$_3$+DMSO): δ10.70 (1H, s), 8.98 (1H, s), 8.80 (1H, s), 7.08-7.00 (1H, d), 7.81-7.76 (2H, t), 7.51-7.49 (1H, d), 7.42-7.36 (3H, dd), 7.27-7.22 (3H, m), 7.14-7.08 (1H, t), 7.02-7.00 (2H, d), 6.48-6.40 (1H, dd,), 6.30-6.26 (1H, d), 5.82-5.80 (2H, d), 2.40 (3H, s).

Example 10

Oxalate of N-{4-[3-chloro-4-(3-fluoro-benzyloxy) phenylamino]-quinazolin-6-yl}-acrylamide 1.0 g (2.23 mmol) of the compound N-{4-[3-chloro-4-(3-fluoro-benzyloxy)phenyl-amino]-quinazolin-6-yl}-acrylamide prepared according to Example 1 was dissolved in 20 mL of methanol and was stirred in an ice-water bath. 2 ml of methanol solution of oxalic acid (990 mg) was added dropwise to the system slowly, and a large amount of yellow solid precipitated from the system. The stir was stopped after 45 min. The solid was collected by filtration, washed with water and dried to obtain 530 mg (0.98 mmol) of Kelly solid, which was identified as the oxalate of N-{4-[3-chloro-4-(3-fluoro-benzyloxy)phenylamino]-quinazolin-6-yl}-acrylamide with a yield of 44%. MS: 449. mp: 253-256°.

$^1$H-NMR (400 MHz, CDCl$_3$+DMSO): δ9.11 (1H, s), 8.76-8.64 (2H, m), 8.01 (1H, d, J=2.44 Hz), 7.90 (2H, s), 7.71 (1H, dd, J=2.56 Hz, 8.92 Hz), 7.52-7.41 (2H, m), 7.33-7.26 (2H, m), 7.12-7.05 (2H, m), 6.54 (2H, d), 6.12 (1H, t), 5.56 (2H, s), 2.98 (6H, s).

Example 11

Acetate of N-{4-[3-chloro-4-(3-fluoro-benzyloxy) phenylamino]-quinazolin-6-yl}-acrylamide According to the method described in Example 10, the acetic acid (660 mg) was used instead of oxalic acid. The acetate of N-{4-[3-chloro-4-(3-fluoro-benzyloxy)phenylamino]-quinazolin-6-yl}-acrylamide was obtained.

$^1$H-NMR (400 MHz, CDCl$_3$+DMSO): δ8.97 (1H, s), 8.90-8.74 (2H, m), 8.09 (1H, d, J=2.44 Hz), 7.87 (2H, s), 7.72 (1H, dd), 7.52-7.38 (2H, m), 7.40-7.35 (2H, m), 7.29-7.24 (2H, m), 6.58 (2H, d), 6.32 (1H, t), 5.66 (2H, s), 2.10 (3H, s).

Example 12

Valerate of N-{4-[3-chloro-4-(3-fluoro-benzyloxy) phenylamino]-quinazolin-6-yl}-acrylamide According to the method described in Example 10, the valeric acid (1.12 g) was used instead of oxalic acid. The valerate of N-{4-[3-chloro-4-(3-fluoro-benzyloxy)phenylamino]-quinazolin-6-yl}-acrylamide was obtained.

$^1$H-NMR (400 MHz, CDCl$_3$+DMSO): δ8.97 (1H, s), 8.90-8.74 (2H, m), 8.09 (1H, d, J=2.44 Hz), 7.87 (2H, s), 7.72 (1H, dd), 7.52-7.38 (2H, m), 7.40-7.35 (2H, m), 7.29-7.24 (2H, m), 6.58 (2H, d), 6.32 (1H, t), 5.66 (2H, s), 2.28 (3H, t), 1.60 (2H, m), 1.38 (2H, m), 1.00 (31-1, t).

Example 13

Malonate of N-{4-[3-chloro-4-(3-fluoro-benzyloxy) phenylamino]-quinazolin-6-yl}-acrylamide According to the method described in Example 10, the malonic acid (1.14 g) was used instead of oxalic acid. The malonate of N-{4-[3-chloro-4-(3-fluoro-benzyloxy)phenylamino]-quinazolin-6-yl}-acrylamide was obtained.

$^1$H-NMR (400 MHz, CDCl$_3$+DMSO): δ8.97 (1H, s), 8.90-8.74 (2H, m), 8.09 (1H, d, J=2.44 Hz), 7.87 (2H, s), 7.72 (1H, dd), 7.52-7.38 (2H, m), 7.40-7.35 (2H, m), 7.29-7.24 (2H, m), 6.58 (2H, d), 6.32 (1H, t), 5.66 (2H, s), 3.27 (2H, s).

Example 14

Tartrate of N-{4-[3-chloro-4-(3-fluoro-benzyloxy) phenylamino]-quinazolin-6-yl}-acrylamide According to the method described in Example 10, the tartaric acid (1.65 g) was used instead of oxalic acid. The tartrate of N-{4-[3-chloro-4-(3-fluoro-benzyloxy)phenylamino]quinazolin-6-yl}-acrylamide was obtained.

Elementary analysis (C$_{28}$H$_{24}$ClFN$_4$O$_3$):
Calculated value: C, 56.15%; H, 4.04%; N, 9.35%.
Measured value: C, 56.19%; H, 4.04%; N, 9.33%.

$^1$H-NMR (400 MHz, CDCl$_3$+DMSO): δ8.97 (1H, s), 8.90-8.74 (2H, m), 8.09 (1H, d, J=2.44 Hz), 7.87 (2H, s), 7.72 (1H, dd), 7.52-7.38 (2H, m), 7.40-7.35 (2H, m), 7.29-7.24 (2H, m), 6.58 (2H, d), 6.32 (1H, t), 5.66 (2H, s), 4.55 (2H, s).

Example 15

Triethylamine salt of N-{4-[3-chloro-4-(3-fluoro-benzyloxy)phenyl-amino]-quinazolin-6-yl}-acrylamide 1.0 g (2.23 mmol) of the compound N-{4-[3-chloro-4-(3-fluoro-benzyloxy)phenylamino]-quinazolin-6-yl}-acrylamide prepared according to Example 1 was suspended in 20 mL of methanol and was stirred at the temperature of 35° C. 2.3 mL of triethylamine was added dropwise to the system slowly with stir, and the suspension turned clear gradually. The stir was stopped after 45 min, and the resulting mixture was concentrated, washed with water and dried to obtain 530 mg (0.96 mmol) of Kelly solid, which was identified as the triethylamine salt of N-{4-[3-chloro-4-(3-fluoro-benzyloxy)phenylamino]-quinazolin-6-yl}-acrylamide with a yield of 43%. MS: 449.

$^1$H-NMR (400 MHz, CDCl$_3$+DMSO): δ10.59 (1H, s), 10.07 (1H, s), 8.80 (1H, s), 8.58 (1H, s), 7.95-7.89 (2H, m), 7.79-7.75 (1H, d), 7.67-7.63 (1H, dd), 7.49-7.42 (2H, s), 7.33-7.23 (3H, m), 7.19-7.13 (1H, m), 7.12-7.07 (2H, dm), 6.58-6.42 (1H, m), 6.38-6.35 (1H, d), 5.84 (1H, t,), 5.21 (2H, s), 1.20-1.10 (9H, m).

Example 16

Solubility Test

According to the conventional method for determining the solubility, at the room temperature, a suitable amount of the compound to be tested was placed in 15 mL of water. Then the compound was dissolved by sufficient stir. The solution is placed at room temperature for 3 hours. Then 10 ml of the clear saturated supernatant was transferred into the weighing bottle with the pipette. The solvent was evaporated by heating, and the residue was dried and weighed to obtain the mass of the residue, which was the mass of the solute. After calculation, the solubility of the compound of formula (I) and the salts thereof in water can be obtained. The solubility of the compound to be tested in methanol was determined along the same lines. The results are shown as follows:

| Compound | Solubility in water(/mL) | Solubility in methanol(/mL) |
| --- | --- | --- |
| Compound of formula (I) | <10 ng | <1 mg |
| Hydrochloride | >5 μg | >5 mg |
| Sulfate | >5 μg | >5 mg |
| p-Toluenesulfonate | >7 μg | >7 mg |
| Methanesulfonate | >5 μg | >5 mg |
| Oxalate | >5 μg | >5 mg |
| Tartrate | >7 μg | >7 mg |
| Triethylamine salt | >5 μg | >5 mg |

Example 17

Determination of Drug Absorption in SD Rat (Sprague Dawley Rat)

Intragastric administration (ig): 24 healthy SD rats, male, weighed 200~250 g, grouped into 3 groups randomly, and were administered independently the compound (21.68 mg/kg) prepared according to Example 1, its hydrochloride (23.42 mg/kg) or p-Toluenesulfonate (30 mg/kg) by gavage. The blood samples were collected 0.5, 1.0, 1.5, 2.0, 3.0, 5.0, 7.0, 9.0, 12 and 24 hours after administration, which were then centrifugated respectively to obtain the plasma. The concentration of the drug in the plasma was determined by means of liquid chromatography/tandem mass spectrometer, and the concentration-time curve was obtained.

The main pharmacokinetic parameters were shown in the following table:

| Compound | Dosage (mg/kg) | $T_{max}$ (h) | $C_{max}$ (ng/mL) | $AUC_{0-t}$ (ng·h/mL) | $T_{1/2}$ (h) |
| --- | --- | --- | --- | --- | --- |
| Compound of formula (I) | 21.68 | 0.75 | 32 | 106 | 1.81 |
| Hydrochloride | 23.42 | 2.25 | 289 | 1038 | 1.27 |
| p-Toluenesulfonate | 30 | 3.38 | 333 | 1235 | 1.22 |

Administration by intravenous injection (iv): 8 healthy SD rats, male, weighed 200~250 g were administered p-toluenesulfonate of the compound of formula (I). The blood samples were collected 5 min, 15 min, 0.5, 1.5, 2.0, 3.0, 4.0, 5.0, 7.0 hours after administration, which were then centrifugated respectively to obtain the plasma. The concentration of the drug in the plasma was determined by means of liquid chromatography/tandem mass spectrometer, and the concentration-time curve was obtained.

The main pharmacokinetic parameters were shown in the following table:

| Compound | Dosage (mg/kg) | $T_{max}$ (h) | $C_{max}$ (ng/mL) | $AUC_{0-t}$ (ng·h/mL) | $T_{1/2}$ (h) |
| --- | --- | --- | --- | --- | --- |
| p-Toluenesulfonate | 5 | 0.083 | 1745 | 1860 | 1.55 |

Revised by dosage, calculated by $AUC_{0-t}$, the absolute bioavailability by ig of the compound of Example 1 was 0.95%, and the absolute bioavailability by ig of the hydrochloride of the compound was 9.30%, and the absolute bioavailability by ig of the p-toluenesulfonate of the compound was 11.07%.

Example 18

Determination of the Inhibitory Effect on EGFR Tyrosine Kinases

The plate coated with EGFR tyrosine kinases reaction substrate Poly(Glu, Tyr) 4:1 was washed three times with T-PBS and dried in oven at the temperature of 37° C. Every well was added with the ATP solution diluted with reaction buffer, the compound to be tested with grading concentrations and the tyrosine kinases to be tested in sequence to initiate the reaction. The plate was incubated in a shaker for 1 hour at the temperature of 37° C., and then was washed three times with T-PBS (the phosphate buffer containing 0.05% of Tween with a pH of 7.4). Antibody PY99 was added and the reaction was kept on at 37° C. for 1 hour. The plate was washed three times with T-PBS, HRP labeled goat anti mouse IgG was then added and incubated at 37° C. for 1 hour. The colorimetric solution of OPD (o-phenylenediamine) was added and the mixture was reacted in dark at room temperature for 1-10 min. The reaction was terminated by the addition of 2M of H$_2$SO$_4$. The OD value at wavelength of 492 nm was measured using the VersaMax™ microplate reader (MDC company, USA). The inhibitory effect of the samples on EGFR tyrosine kinases was determined by the following formula:

Inhibition %=[1−(OD Value of the compound to be tested −OD Value of the control without enzyme)/(OD Value of the negative control−OD Value of the control without enzyme)]×100%.

The results indicated: the hydrochloride, the p-toluenesulfonate, methanesulfonate, oxalate and tartrate of the compound of formula (I) possess excellent inhibitory activity of EGFR tyrosine kinases.

Example 19

Determination of the Inhibition of the Proliferation of Tumor Cell Lines

The p-toluenesulfonate or the hydrochloride of the compound of formula (I) obtained in Example 1 was prepared into 5 concentration gradients. According to the live cell tetrazolium (3-(4,5-dimethylthiahiazolo-2-yl)-3,5-di-phenyl tetrazolium bromide, MTT) method, the human epidermatoid squamous cancer cell A431 and human breast cancer cell BT-474 (1×10$^5$) in logarithmic growth period were inoculated in 96-well plates respectively, incubated for 24 hours, and then the solutions of the compound to be tested with different concentrations were added, with three wells for each concentration. A DMSO solvent control well and a blank well were set in the plate. After treated with the compounds at 37° for 72 h, 20 µL of MTT solution (Sigma™, St Louis, Mo., USA) was added into every well. The incubation was continued for 4 h, and 50 µL of triple-expansion solution (10% SDS-5% of isobutyl alcohol-0.01 mol/L of HCl) was added. The plate was placed in the incubator overnight. The OD value was measured by the microplate reader at wavelength of 570 nm. The inhibitory effect of the compounds on the growth of the cells can be determined by the following formula:

Inhibition(%)=(OD Value of the solvent control−OD Value of the compound to be tested)/OD Value of the solvent control×100%, The IC$_{50}$ values were calculated according to the Logit method.

Results: The IC$_{50}$ values of the p-toluenesulfonate of the compound of formula (I) for human epidermatoid squamous cancer cell A431 and human breast cancer cell BT-474 were 0.73 µM and 0.42 µM, respectively. The IC$_{50}$ values of the hydrochloride of the compound of formula (I) for human epidermatoid squamous cancer cell A431 and human breast cancer cell BT-474 were 0.84 µM and 0.46 µM, respectively.

Example 20

1. Determination of the Anti-Tumor Effect on the Human Epidermatoid Squamous Cancer A431 Transplanted to the BALB/cA Nude Rat A well-developed solid tumor A431 was selected and incised into several bits of an even size of 2-3 mm, with one bit being inoculated subcutaneously to the right armpit of each of the BALB/cA nude rats using trocar. 7 days after inoculation, the rats were grouped randomly and were administrated with the compounds by gavage through mouth for 13 days continuously. The major axis (a) and the minor axis (b) of the tumors were measured with a vernier caliper every 4 days. According to the formula V=ab$^2$/2, the tumor volume (mm$^3$) could be calculated. The tested animals were neck-off killed 23 days after the inoculation, and anatomized to obtain the tumors. The tumors were weighed and the inhibitory effect of the compounds to be tested was figured out.

The results are shown in the table below, which indicated that the p-toluenesulfonate of the compound of formula (I) have the significant inhibitory effect on the tumors.

| Groups | Dosage (mg/kg) | Administration route | Number of animals Beginning | End | Weight of animals(g) (without tumor) | Weight of tumors (g) $\bar{x} \pm SD$ | inhibition for tumor % |
|---|---|---|---|---|---|---|---|
| Solvent control | 25 mL/kg | ig | 7 | 7 | 22.40 ± 2.81 | 1.13 ± 0.18 | 0 |
| p-toluenesulfonate | 25 | ig | 5 | 5 | 21.58 ± 2.18 | 0.79 ± 0.20 | 29.99 |
|  | 50 | ig | 5 | 5 | 22.05 ± 1.59 | 0.71 ± 0.20 | 37.15 |
|  | 100 | ig | 5 | 5 | 22.35 ± 1.92 | 0.58 ± 0.21 | 48.65 |

2. Determination of the Anti-Tumor Effect on the Human Ovarian Cancer SKOV-3 Transplanted to the BALB/cA Nude Rat A tumor SKOV-3 in vigorous growth period was selected and incised into several bits of an even size of about 1.5 mm$^3$, which was inoculated subcutaneously to the right armpit of the BALB/cA nude rats using trocar under sterile condition. The diameters of the transplanted tumors were measured with a vernier caliper. The animals were grouped randomly when the tumors reached a size of 80-100 mm$^3$. The tested animals of the group receiving the compounds to be tested were administrated with the compounds by gavage through mouth once daily for 3 weeks continuously. The positive control drug MMC (Mitomycin) was administered by intravenous injection once on the first day with a dose of 5 mg/kg. The negative control group was administrated with 0.5% CMC-Na (Carboxymethyl Cellulose Sodium) with a dose of 0.2 mL/per rat. The major axis (a) and the minor axis (b) of the tumors were measured twice every week and the rats were weighed at the same time. According to the formula V=ab$^2$/2, the tumor volume (mm$^3$) could be calculated, based on which the relative tumor volume (RTV) was determined (Formula: RTV=V$_t$/V$_0$, wherein V$_0$ represents the tumor volume measured at the grouping time (i.e. d$_0$), and V$_t$ represents the tumor volume measured each time). The relative tumor proliferation rate T/C (%) was chosen here to evaluate the anti-tumor activity, which can be calculated according to the following formula:

$$T/C(\%)=(T_{RTV}/C_{RTV})\times 100\%$$

T$_{RTV}$: RTV of the group receiving the compounds to be tested; C$_{RTV}$: RTV of negative control group The standard for evaluating the effectiveness: T/C (%)>60% means ineffective and T/C (%)≦60% means effective.

The results are shown in the table below, which indicate that the p-toluenesulfonate of the compound of formula (I) has the conspicuous tumor inhibitory effect.

| Groups | Dosage, Administration route | | Number of animals | | Volume of tumor (mm³) | | | T/C (%) |
|---|---|---|---|---|---|---|---|---|
| | | | Start | End | $V_0$ | $V_{21}$ | RTV | |
| 0.5% CMC-Na | 0.2 mL/per rat | ig | 12 | 12 | 85 ± 35 | 638 ± 339 | 9.6 ± 5.4 | |
| MMC | 5 mg/kg | iv | 6 | 6 | 83 ± 13 | 258 ± 77 | 3.1 ± 0.5 | 32.0 |
| p-toluenesulfonate | 200 mg/kg | ig | 6 | 6 | 86 ± 13 | 303 ± 72 | 3.5 ± 0.8 | 36.9 |
| p-toluenesulfonate | 100 mg/kg | ig | 6 | 6 | 87 ± 41 | 345 ± 88 | 4.3 ± 1.3 | 45.0 |
| p-toluenesulfonate | 50 mg/kg | ig | 6 | 6 | 79 ± 28 | 421 ± 89 | 5.1 ± 1.7 | 53.0 |

$V_0$ represents the tumor volume before the administration, and $V_{21}$ represents the tumor volume after 3 weeks of continuous administration Example 21

Toxicity Test of Long-Term Administration 130 healthy SD rats, male, weighed 200~250 g, were grouped into 26 groups randomly, and were administered independently with the hydrochloride, the p-toluenesulfonate, the methanesulfonate, the oxalate or the tartrate of the compound of formula (I) by gavage for 4 weeks continuously. Five test groups with the dose of 20, 50, 100, 500 and 800 mg/(kg·day) respectively and a solvent control group were set. The results after four weeks of administration indicated that: the rats of the five test groups with the dose of 20, 50, 100, 500 and 800 mg/(kg-day) respectively showed no abnormality in physical signs, appearance, behaviors, activities or shape of dejecta. Said rats had a normal food intake, and the weight and weight growth of the rats were basically similar to the control group with no statistical difference. The inspection results of the test groups of hematology, blood biochemistry, cardiogram, body temperature and urine were similar to those of the control group, the varieties of which were in the normal range, indicating that the salt forms of the compound of formula (I) possessed low toxicity and safety.

Example 22

Pharmaceutical Composition

The capsules containing the hydrochloride of N-{4-[3-chloro-4-(3-fluoro-benzyloxy)phenylamino]-quinazolin-6-yl}-acrylamide were prepared from the following components:

| The hydrochloride of the compound of formula (I) | 15 g |
|---|---|
| Starch | 15 g |
| Lactose | 30 g |
| PVPP | 2.5 g |
| PVP | 2.5 g |
| Talcum powder | 3 g |
| Sodium dodecyl sulfate | 4 g |

According to the conventional method, the hydrochloride of the compound of formula (I) and the starch were mixed and sieved and then evenly mixed with other components mentioned above and filled into general gelatin capsules.

Example 23

Pharmaceutical Composition

The tablets containing the p-toluenesulfonate of N-{4-[3-chloro-4-(3-fluoro-benzyloxy)phenylamino]-quinazolin-6-yl}-acrylamide were prepared from the following components:

| The p-toluenesulfonate of the compound of formula (I) | 20 g |
|---|---|
| Starch | 20 g |
| Lactose | 40 g |
| PVPP | 3 g |
| PVP | 3 g |
| Talcum powder | 1.6 g |
| Sodium dodecyl sulfate | 5 g |

According to the conventional method, the p-toluenesulfonate of the compound of formula (I) and the starch were mixed and sieved and then evenly mixed with other components mentioned above, and pressed into tablets directly.

All documents referred to throughout this application are hereby incorporated in their entireties by reference herein, as if each of them is individually incorporated. Further, it would be appreciated that, in light of the above teaching, the skilled person in the art may make various changes or modifications to the invention, and these equivalents would still be within the scope of the invention defined by the appended claims of the application.

The invention claimed is:

1. A pharmaceutically acceptable salt of the compound of formula (I):

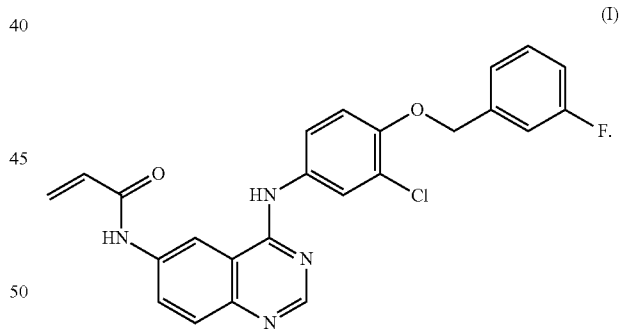

(I)

2. The salt of claim 1, wherein the salt is an acid addition salt formed from the compound of formula (I) with an inorganic or organic acid, or a base addition salt formed from the compound of formula (I) with an inorganic or organic base.

3. The salt of claim 2, wherein the salt is an acid addition salt.

4. The salt of claim 3, wherein the acid addition salt is selected from the group consisting of hydrobromide, hydrochloride, sulfate, bisulfate, carbonate, bicarbonate, sulfite, phosphate, biphosphate, borate, acetate, oxalate, malonate, valerate, benzoate, p-toluenesulfonate, methanesulfonate, tartrate, lactate, benzoate, toluate, citrate, maleate, fumarate, malate, pamoate, salicylate, vanillate, mandelate and succinate.

5. The salt of claim 4, wherein the acid addition salt is selected from the group consisting of hydrochloride, sulfate, phosphate, carbonate, p-toluenesulfonate, methanesulfonate, benzoate, salicylate, oxalate, acetate, valerate, malonate and tartrate.

6. The salt of claim 1, wherein the salt is an acid addition salt and the acid addition salt is hydrochloride or p-toluenesulfonate.

7. The salt of claim 2, wherein the salt is a base addition salt.

8. The salt of claim 7, wherein the base addition salt is selected from the group consisting of alkali metal salt, alkali earth metal salt, quaternary ammonium cation salt and amine salt.

9. The salt of claim 8, wherein the base addition salt is selected from the group consisting of sodium salt, potassium salt, calcium salt, magnesium salt, tetramethyl quaternary ammonium salt, tetraethyl quaternary ammonium salt, methylamine salt, dimethylamine salt, trimethylamine salt, triethylamine salt and ethylamine salt.

10. The salt of claim 9, wherein the base addition salt is triethylamine salt.

11. A process for preparing the salt as defined in claim 1 comprising the steps of:
   (a) dissolving the compound of formula (I) in an organic solvent, and adding dropwise an acid-containing solvent or a base-containing solvent with stirring; and
   (b) filtering the resulting mixture directly or after concentrating, to obtain a solid; water-washing, and drying the solid to obtain the salt.

12. A process of claim 11, wherein the organic solvent is selected from the group consisting of methanol, ethanol, ethyl acetate, tetrahydrofuran, triethylamine, diethyl ether, 1,4-dioxane and a combination thereof.

13. A pharmaceutical composition comprising a pharmaceutically acceptable salt of the compound of formula (I):

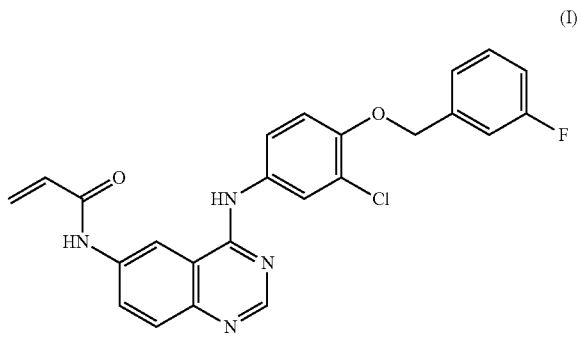 [SMILES: C=CC(=O)Nc1ccc2ncnc(Nc3ccc(OCc4cccc(F)c4)c(Cl)c3)c2c1]

(I)

and a pharmaceutically acceptable carrier.

14. The pharmaceutical composition of claim 13, wherein the salt is an acid addition salt formed from the compound of formula (I) with an inorganic or organic acid, or a base addition salt formed from the compound of formula (I) with an inorganic or organic base.

15. The pharmaceutical composition of claim 14, wherein the salt is an acid addition salt.

16. The pharmaceutical composition of claim 15, wherein the acid addition salt is selected from the group consisting of hydrobromide, hydrochloride, sulfate, bisulfate, carbonate, bicarbonate, sulfite, phosphate, biphosphate, borate, acetate, oxalate, malonate, valerate, benzoate, p-toluenesulfonate, methanesulfonate, tartrate, lactate, benzoate, toluate, citrate, maleate, fumarate, malate, pamoate, salicylate, vanillate, mandelate and succinate.

17. The pharmaceutical composition of claim 16, wherein the acid addition salt is selected from the group consisting of hydrochloride, sulfate, phosphate, carbonate, p-toluenesulfonate, methanesulfonate, benzoate, salicylate, oxalate, acetate, valerate, malonate and tartrate.

18. The pharmaceutical composition of claim 13, wherein the salt is an acid addition salt and the acid addition salt is hydrochloride or p-toluenesulfonate.

19. The pharmaceutical composition of claim 13, wherein the salt is a base addition salt.

20. The pharmaceutical composition of claim 19, wherein the base addition salt is selected from the group consisting of alkali metal salt, alkali earth metal salt, quaternary ammonium cation salt and amine salt.

21. The pharmaceutical composition of claim 20, wherein the base addition salt is selected from the group consisting of sodium salt, potassium salt, calcium salt, magnesium salt, tetramethyl quaternary ammonium salt, tetraethyl quaternary ammonium salt, methylamine salt, dimethylamine salt, trimethylamine salt, triethylamine salt and ethylamine salt.

22. The pharmaceutical composition of claim 21, wherein the base addition salt is triethylamine salt.

* * * * *